US011209411B2

(12) United States Patent
Cooks et al.

(10) Patent No.: US 11,209,411 B2
(45) Date of Patent: Dec. 28, 2021

(54) METHODS FOR ANALYZING STABILITY OF AN ACTIVE PHARMACEUTICAL INGREDIENT

(71) Applicant: Purdue Research Foundation, West Lafayette, IN (US)

(72) Inventors: Robert Graham Cooks, West Lafayette, IN (US); Roy Helmy, Kenilworth, NJ (US); Yangjie Li, West Layfayette, IN (US); Yong Liu, Kenilworth, NJ (US)

(73) Assignee: Purdue Research Foundation, West Lafayette, IN (US)

( * ) Notice: Subject to any disclaimer, the term of this patent is extended or adjusted under 35 U.S.C. 154(b) by 205 days.

(21) Appl. No.: 16/245,703

(22) Filed: Jan. 11, 2019

(65) Prior Publication Data
US 2019/0219555 A1    Jul. 18, 2019

Related U.S. Application Data

(60) Provisional application No. 62/616,811, filed on Jan. 12, 2018.

(51) Int. Cl.
*G01N 33/15* (2006.01)
*H01J 49/04* (2006.01)
*H01J 49/00* (2006.01)

(52) U.S. Cl.
CPC .......... *G01N 33/15* (2013.01); *H01J 49/0027* (2013.01); *H01J 49/0445* (2013.01)

(58) Field of Classification Search
CPC ... H01J 49/0027; H01J 49/0445; G01N 33/15
See application file for complete search history.

(56) References Cited

U.S. PATENT DOCUMENTS 8,304,718 B2    11/2012 Ouyang et al.
8,410,431 B2    4/2013 Ouyang et al.
(Continued)

FOREIGN PATENT DOCUMENTS

WO    2009/102766 A1    8/2009

OTHER PUBLICATIONS

Bain, R. M., Pulliam, C. J., Thery, F., & Cooks, R. G. (2016). Accelerated chemical reactions and organic synthesis in Leidenfrost droplets. Angewandte Chemie International Edition, 55(35), 10478-10482. (Year: 2016).*

(Continued)

*Primary Examiner* — Samuel P Siefke
*Assistant Examiner* — Oyeleye Alexander Alabi
(74) *Attorney, Agent, or Firm* — Brown Rudnick LLP; Adam M. Schoen (57) ABSTRACT

The invention generally relates to methods for analyzing stability of an active pharmaceutical agent. In certain aspects, the methods involve obtaining an active pharmaceutical agent, and distributing the active pharmaceutical agent into one or more microdroplets. The one or more microdroplets including the active pharmaceutical agent are then subjected to one or more conditions that force degradation of the active pharmaceutical agent in each of the one or more microdroplets. The one or more microdroplets are then analyzed to determine a ratio of the active pharmaceutical agent to that of a degradation product of the active pharmaceutical agent, thereby analyzing stability of an active pharmaceutical agent.

19 Claims, 9 Drawing Sheets

(56) References Cited

U.S. PATENT DOCUMENTS

| | | | |
|---|---|---|---|
| 9,500,623 B2 | 11/2016 | Cooks et al. | |
| 2004/0151670 A1* | 8/2004 | Blondino | A61P 29/00 424/45 |
| 2013/0280819 A1* | 10/2013 | Cooks | H01J 49/04 436/173 |
| 2014/0224981 A1 | 8/2014 | Owen et al. | |
| 2017/0349547 A1 | 12/2017 | Cooks et al. | |
| 2018/0043327 A1 | 2/2018 | Cooks et al. | |

OTHER PUBLICATIONS

Bain, Ryan M., et al. "Accelerated chemical reactions and organic synthesis in Leidenfrost droplets." Angewandte Chemie International Edition 55.35 (2016): 10478-10482. (Year: 2016).*

Carroll, 1975, Atmospheric Pressure Ionization Mass Spectrometry: Corona Discharge Ion Source for Use in Liquid Chromatograph-Mass Spectrometer-Computer Analytical System, Anal. Chem. 47:2369-2373.

Cody, 2005, Versatile New Ion Source for the Analysis of Materials in Open Air under Ambient Conditions, Anal. Chem., 77:2297-2302.

Cotte-Rodriguez, 2006, Non-proximate detection of explosives and chemical warfare agent simulants by desorption electrospray ionization mass spectrometry, Chem. Commun., 28:2968-2970.

Fenn, 1989, Electrospray Ionization for Mass Spectrometry of Large Biomolecules, Science 246:64-71.

Gao, 2006, Handheld Rectilinear Ion Trap Mass Spectrometer, Anal. Chem. 78:5994-6002.

Hendricks, 2014, Autonomous in-situ analysis and real-time chemical detection using a backpack miniature mass spectrometer: concept, instrumentation development, and performance, Anal. Chem., 86:2900-2908.

Karas, 2000, Nano-electrospray ionization mass spectrometry: addressing analytical problems beyond routine, Fresenius J. Anal. Chem., 366:669-676.

Kogelschatz, 2003, Dielectric-barrier Discharges: Their History, Discharge Physics, and Industrial Applications, Plasma Chem. and Plasma Processing, 23:1-46.

Laiko, 2000, Atmospheric Pressure Matrix-Assisted Laser Desoprtion/Ionization Mass Spectrometry, Analytical Chemistry, 72:652-657.

Li, 2014, Mini 12, Miniature Mass Spectrometer for Clinical and Other Applications—Introduction and Characterization, Anal. Chem., 86:2909-2916.

Pan, 2004, Nanoelectrospray Ionization of Protein Mixtures: Solution pH and Protein pI, Anal. Chem., 76:1165-1174.

Shiea, 2005, Electrospray-assisted laser desorption/ionization mass spectrometry for direct ambient analysis of solids, J. Rapid Comm in Mass Spectrometry, 19:3701-3704.

Takats, 2004, Electronsonic Spray Ionization. A Gentle Technique for Generating Folded Proteins and Protein Complexes in the Gas Phase and for Studying Ion-Molecule Reactions at Atmospheric Pressure, Anal. Chem., 76(14):4050-4058.

Tanaka, 1988, Protein and Plymer Analyses up to m/z 100 000 by Laser Ionization Time-of-Flight Mass Spectrometry, Rapid Commun. Mass Spectrom, 2:151-153.

Yamashita, 1984, Electrospray Ion Source. Another Variation on the Free-Jet Theme, J. Phys. Chem., 88:4451-4459.

* cited by examiner

METHODS FOR ANALYZING STABILITY OF AN ACTIVE PHARMACEUTICAL INGREDIENT

RELATED APPLICATION

The present application claims the benefit of and priority to U.S. provisional application No. 62/616,811, filed Jan. 12, 2018, the content of which is incorporated by reference herein in its entirety.

FIELD OF THE INVENTION

The invention generally relates to methods for analyzing stability of an active pharmaceutical ingredient.

BACKGROUND

Forced degradation studies of APIs are an important aspect of pharmaceutical development. The aim of such studies is to selectively probe chemical reactivity of active pharmaceutical ingredients (APIs) to understand the degradation chemistry that is possible in formulations. Further, the rates of chemical reactions in these studies yield some insight into shelf life prediction. Once possible mechanisms are understood, formulation strategies can be developed to minimize the degradation chemistry and enable design of a stable formulation product. Ultimately, full understanding of potential degradation chemistry is a foundation of quality-by-design to enable successful development drug products at the molecular level.

Acceleration of degradation is important to shorten the time required to follow the actual degradation processes in actual formulations. The established forced degradation methods still take considerable time, typically being performed over the course of 1-7 days. The reaction mixtures are then analyzed by HPLC to confirm the separation of the API from the degradation products. The results are used to assess the stability of the compound under each stress condition and to study the corresponding degradation mechanism. The study presented herein explores a method to more rapidly assess degradation chemistry of APIs under hydrolysis and oxidation conditions.

SUMMARY

The invention recognizes and takes advantage of the fact that rates of chemical reactions can be accelerated in small droplets or thin films over corresponding bulk rates. Certain aspects of the invention employ the Leidenfrost effect to create small levitated droplets. By pouring a liquid onto a surface at a temperature significantly greater than the boiling point of the liquid, levitating solution droplets can be created from which solvent gradually evaporates. These mm-sized droplets last for some minutes and when used as reaction vessels for APIs they force degradation to be even faster than would be the case under traditional forced degradation conditions as is shown herein.

Accordingly, certain aspects of the invention provide methods for analyzing stability of an active pharmaceutical ingredient. The methods involve obtaining an active pharmaceutical ingredient, and distributing the active pharmaceutical ingredient into one or more microdroplets. The one or more microdroplets including the active pharmaceutical ingredient are then subjected to one or more conditions that force degradation of the active pharmaceutical ingredient in each of the one or more microdroplets. The one or more microdroplets are then analyzed to determine a ratio of the active pharmaceutical ingredient to that of a degradation product of the active pharmaceutical ingredient, thereby analyzing stability of an active pharmaceutical ingredient. Exemplary conditions that force degradation of the active pharmaceutical ingredient may be acid addition, base addition, addition of an agent that causes radical initiation, peroxide addition, heat, or any combination thereof.

In other aspects, the invention provides methods for analyzing stability of a modified formulation that includes an active pharmaceutical ingredient. Such methods may involve obtaining a modified formulation that includes an active pharmaceutical ingredient, and distributing the modified formulation that includes the active pharmaceutical ingredient into one or more microdroplets. The one or more microdroplets including the modified formulation that includes the active pharmaceutical ingredient are then subjected to one or more conditions that force degradation of the modified formulation that comprises the active pharmaceutical ingredient in each of the one or more microdroplets. The one or more microdroplets are then analyzed to determine a ratio of the active pharmaceutical ingredient in the modified formulation to presence of a degradation product of the active pharmaceutical ingredient the modified formulation, thereby analyzing stability of an active pharmaceutical ingredient. The methods may further involve determining whether the modified formulation that comprises the active pharmaceutical ingredient slows degradation of the active pharmaceutical ingredient as compared to an unmodified formulation that comprises the active pharmaceutical ingredient.

Numerous different approaches or techniques may be used to distribute the active pharmaceutical agent in any formulation into one or more microdroplets, such as pneumatic spraying, Leidenfrost-levitated microdroplets, or thin film technology. In certain embodiments, the one or more microdroplets are Leidenfrost-levitated microdroplets. Leidenfrost-levitated microdroplets and techniques for forming such droplets are described for example in Cooks et al. (U.S. patent application Ser. No. 15/613,520), the content of which is incorporated by reference herein in its entirety. In certain embodiments, the one or more microdroplets are Leidenfrost-levitated microdroplets which are maintained at a constant volume. The one or more Leidenfrost-levitated microdroplets may be maintained at a constant volume by introducing droplets of pure solvent to the Leidenfrost-levitated microdroplet. In certain embodiments, a rate at which the droplets of the pure solvent are introduced to the Leidenfrost-levitated microdroplet is dependent on an evaporation rate of the Leidenfrost-levitated microdroplets.

In other embodiments, the one or more microdroplets are generated by a pneumatic spray device and forced degradation of the API can occur and be accelerated within those microdroplets. Generating such microdroplets is described for example in Cooks et al. (U.S. patent application Ser. No. 15/673,658), the content of which is incorporated by reference herein in its entirety.

Numerous analytical techniques may be used to analyze the one or more microdroplets to determine a ratio of the active pharmaceutical ingredient to that of a degradation product of the active pharmaceutical ingredient. Exemplary techniques include absorption spectroscopy, fluorescence spectroscopy, or NMR spectroscopy. In certain embodiments, analyzing the one or more microdroplets to determine a ratio of the active pharmaceutical ingredient to that of a degradation product of the active pharmaceutical ingredient is by a mass spectrometry technique.

Methods of the invention may further involve determining an acceleration factor of degradation of the active pharmaceutical ingredient in the one or more microdroplets by measuring time required to convert the active pharmaceutical agent to a fixed amount of the degradation product as determined by peak intensities in a mass spectrum compared to corresponding time for a bulk forced degradation of the active pharmaceutical ingredient. Methods of the invention may further involve determining an acceleration factor of degradation of the active pharmaceutical ingredient in the one or more microdroplets by measuring of a rate constant for conversion of the active pharmaceutical ingredient to degradation products compared to a corresponding rate constant for a bulk forced degradation of the active pharmaceutical ingredient.

BRIEF DESCRIPTION OF THE DRAWINGS

FIGS. 1A-B show a comparison of traditional forced degradation method in bulk solution and the accelerated forced degradation method in Leidenfrost droplets under similar conditions and temperatures to achieve the same extent of degradation in the subsequent MS analysis. The data shown are for tetracycline (TC).

DETAILED DESCRIPTION

Forced degradation is an accelerated method of studying the stability of pharmaceuticals in order to indicate analytical methods suitable to develop and design of proper storage conditions for both drug substances and drug products and provide essential knowledge for formulation development. Traditional forced degradation methods take 1-3 days and are followed by LC/MS product analysis. As shown herein, forced degradation was accelerated in Leidenfrost droplets and the reaction products were characterized, for example by nanospray MS. The reaction/analysis sequence could be completed within minutes. Acid degradation of tetracycline and hydrochlorothiazide and oxidative degradation of trifluoperazine in Leidenfrost droplets showed the same reactions as seen in bulk experiments. Acceleration factors (ratio of droplet vs. bulk rate constants) for the three APIs under the chosen conditions were between 20 and 180. The role played by the large surface/volume ratio in Leidenfrost droplets in accelerated degradation and prospects for even faster automated multiplexed analysis and for use of Leidenfrost microdroplet reactors for scaled-up accelerated synthesis are of note.

Particularly, the degradation of three APIs in Leidenfrost droplets is exemplified, under conditions of constant volume achieved by adding make-up solvent automatically via a syringe pump during the levitation period. The data were compared with the degradation of the corresponding bulk material under similar conditions of solvent and temperature. In both droplet and bulk, degradation products are monitored by mass spectrometry and the ratio of products to reactants was used to infer the extent of reaction (Table 1).

TABLE 1

Degradation of APIs under Leidenfrost vs conventional forced degradation conditions

| API, degradation conditions, solutions | | | Bulk Temp | Bulk Time | Leidenfrost Temp[a] | Leidenfrost Time | Set Ratio | Accel. Factor[b] |
|---|---|---|---|---|---|---|---|---|
| 450 µg/mL Tetracycline (TC) | 0.1M HCl | 90% methanol-10% $H_2O$ | 40° C. | 3 h | 40° C. | 60 s | 4% | ~180 |
| 450 µg/mL Hydrochlorothiazide (HCTZ)[#] | 0.5M HCl | 90% propanol-10% $H_2O$ | 80° C. | 3 h | 80° C. | 40 s | 2.5% | ~270 |
| 45 µg/mL Trifluoperazine (TFP) | 0.3% $H_2O_2$ | 90% methanol-10% $H_2O$ | 40° C. | 1.5 h | 40° C. | 180 s | 3% | ~20 |

[#]HCTZ was examined without adding make-up solvent.

The measurement of the time required to achieve the same product/reagent ion abundance ratio is a good measure of the acceleration factor. This study also followed the kinetics of dissociation.

Figure 1A:
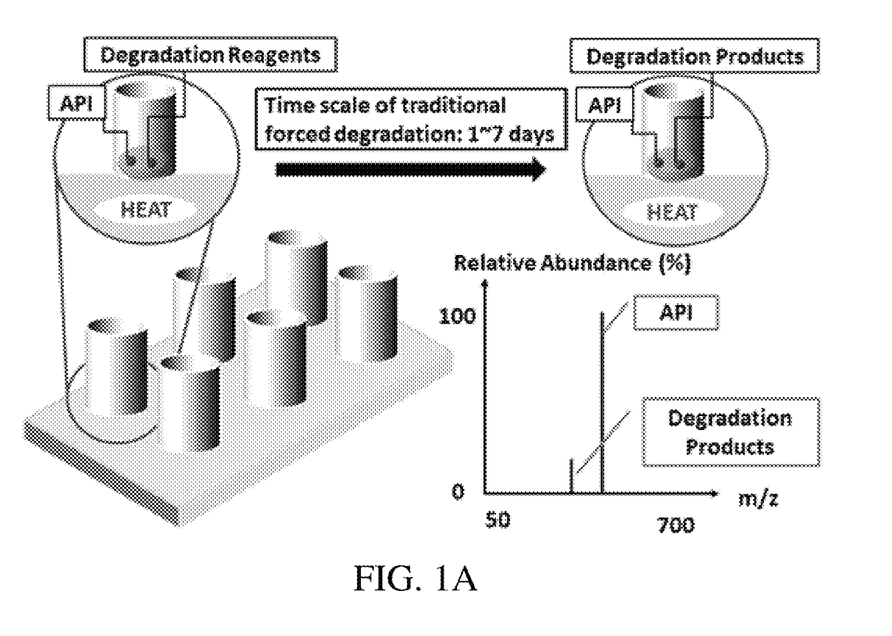
FIG. 1A is traditional forced degradation in a bulk reaction over 1-7 days.
Figure 1B:
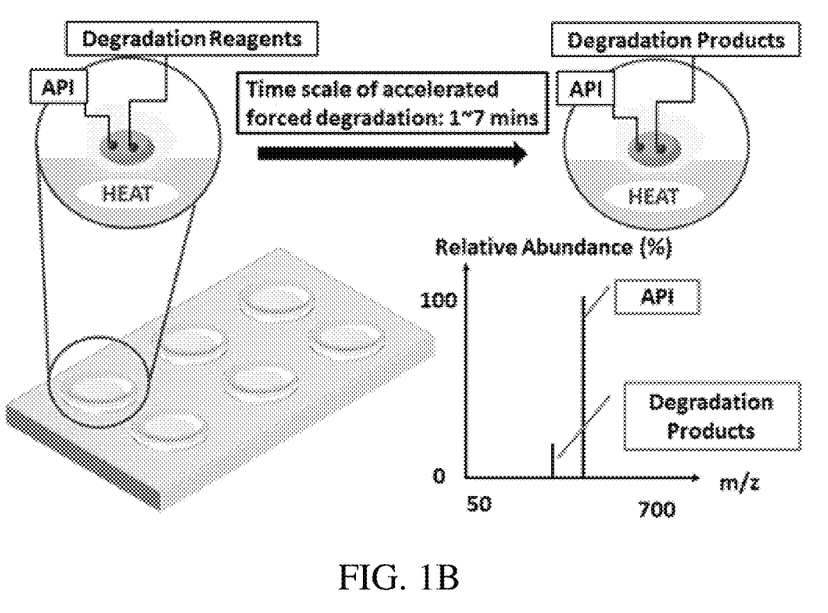
FIG. 1B is an accelerated forced degradation in levitated Leidenfrost droplets over 1-7 minutes.

Traditional forced degradation was performed by preparing a stock stress solution of hydrochloric acid or hydrogen peroxide, and a stock solution of the compound of interest (the API). Then the solutions were mixed and allowed to react at a set temperature for a set period of time (FIG. 1A). The composition of the final reaction mixture was analyzed by nanospray MS and the data for the bulk phase experiments are given in Table 1. Likewise, the Leidenfrost reaction mixture was made by the same method, then instead of letting the mixed solution age at a set temperature, it was dropped into a ceramic well which was placed on hot plate held at a temperature of 540° C. to form a much cooler Leidenfrost droplet (FIG. 1B). Comparison of the bulk traditional forced degradation with the Leidenfrost droplet reaction (accelerated forced degradation) for tetracycline (TC) is illustrated in FIGS. 1A-B. Compared to the traditional forced degradation method, not only is the reaction accelerated by a factor of 180 but the subsequent analysis by mass spectrometry (MS) is faster than HPLC/MS used in the traditional method. Here, both bulk and Leidenfrost products are analyzed by using nanospray MS.

Figure 2A:
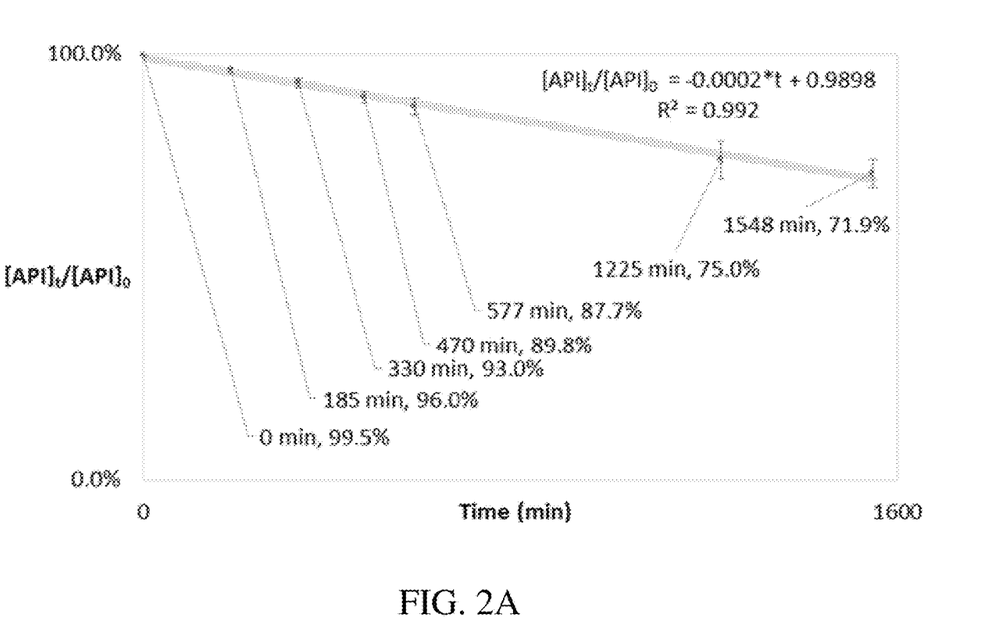
FIGS. 2A-B are graphs showing kinetic profiles for acid degradation of Tetracycline (TC) (0.45 mg/mL TC and 0.1 M HCl in 90% methanol-10% $H_2O$) examined at the same temperature (FIG. 2A) in bulk and (FIG. 2B) in Leidenfrost droplets.
Figure 2B:
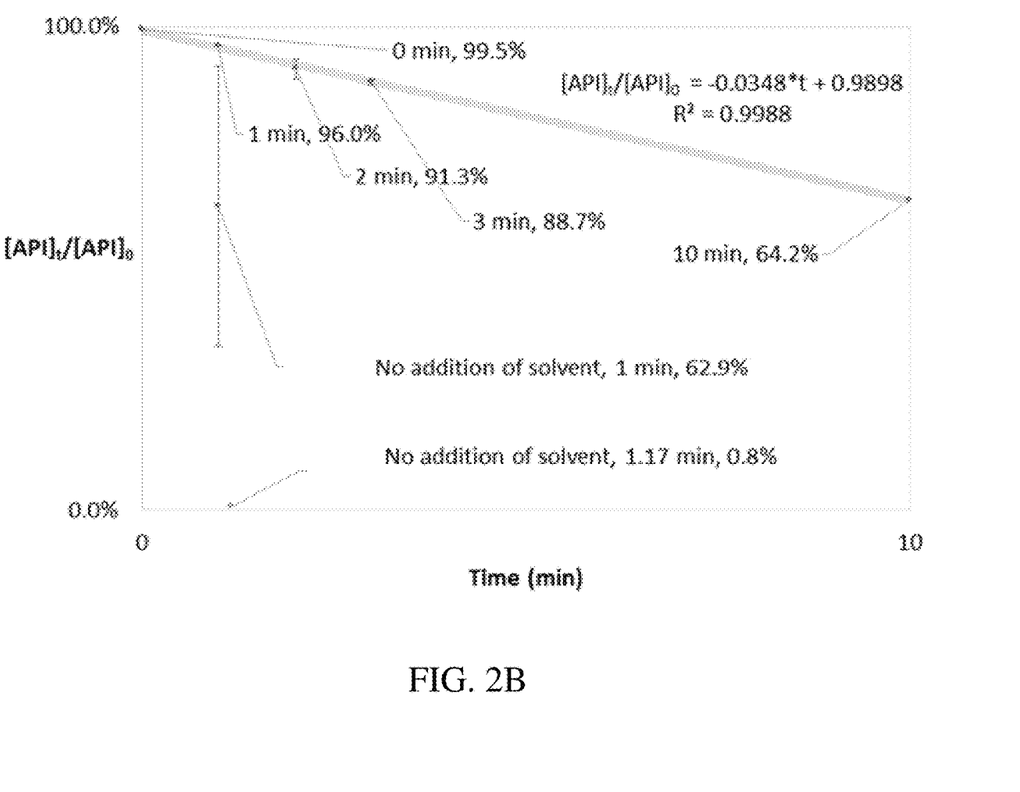

The results for acid degradation of tetracycline (TC) are shown in FIGS. 2A-B. Note that the acceleration factor for tetracycline is unusually high compared to other accelerated reactions in Leidenfrost droplets. This could be due to the fact that water is eliminated during the evaporation of solvent in the Leidenfrost experiment driving the equilibrium towards degradation.

Comparison of the kinetic profiles of tetracycline degradation in acidic condition in bulk solution and in Leidenfrost droplets confirms that the degradation occurs at very different rates. (FIGS. 2A-B). Each data points represents information from three (in FIG. 2B) or four (in FIG. 2A) parallel trials. The x-intercept is smaller than 100% since timing started about 0.5 min after the solutions were added. Note that a comparison experiment has been done where no solvent is added in the Leidenfrost experiment (to maintain a constant droplet volume). In this case the droplet was collected and analyzed before it had completely evaporated (ca. 1 min). MS data showed that in this comparison experiment the degradation is more extensive (63% at 60 s) which indicates again that the large surface/volume ratio in the Leidenfrost droplet contributes to the acceleration. At about 70s after adding the mixture into the hot well, the diameter of the droplet had shrunk to less than 1 mm, and the MS showed that almost all the API has been degraded. This finding suggests that a modified Leidenfrost droplet method could be used to prepare small quantities of the API degradates.

Figure 3A:
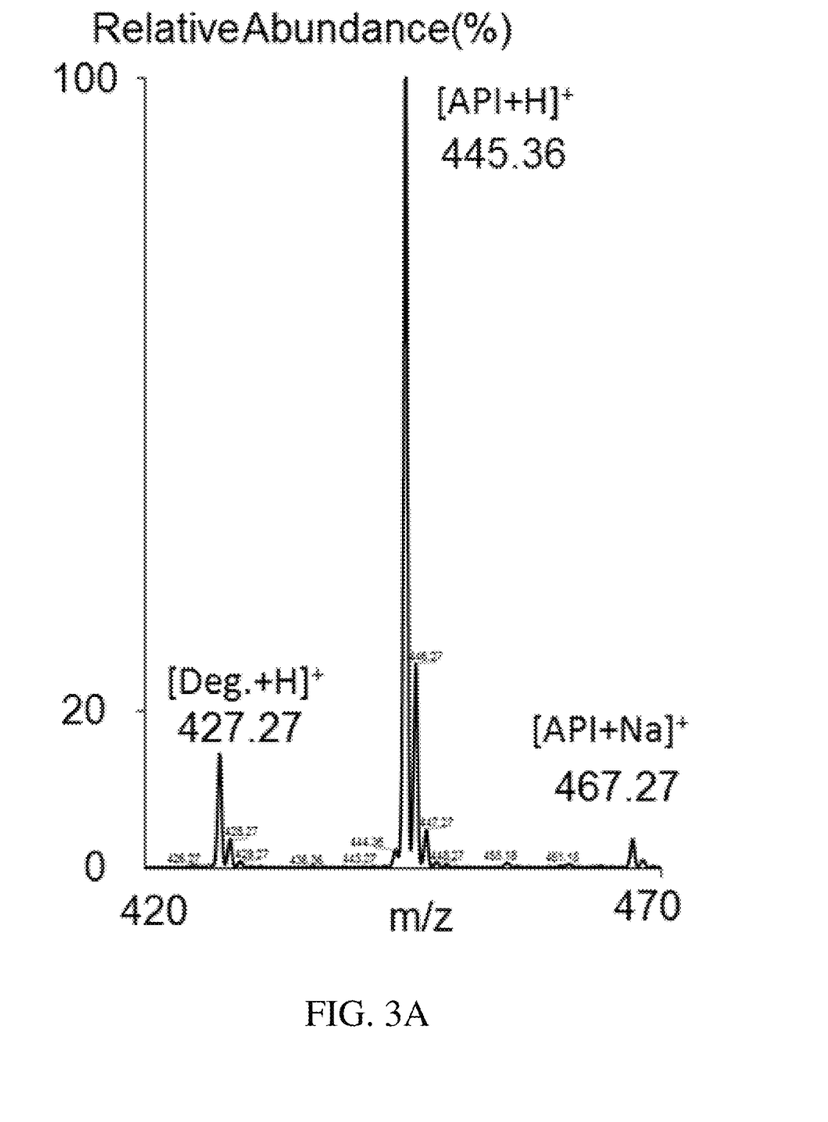
FIGS. 3A-B are mass spectra showing an MS of reaction system of Tetracycline degradation under acidic conditions (0.45 mg/mL tetracycline and 0.1 M HCl in 90% methanol: 10% water) (FIG. 3A) in bulk (FIG. 3B) in Leidenfrost droplet.
Figure 3B:
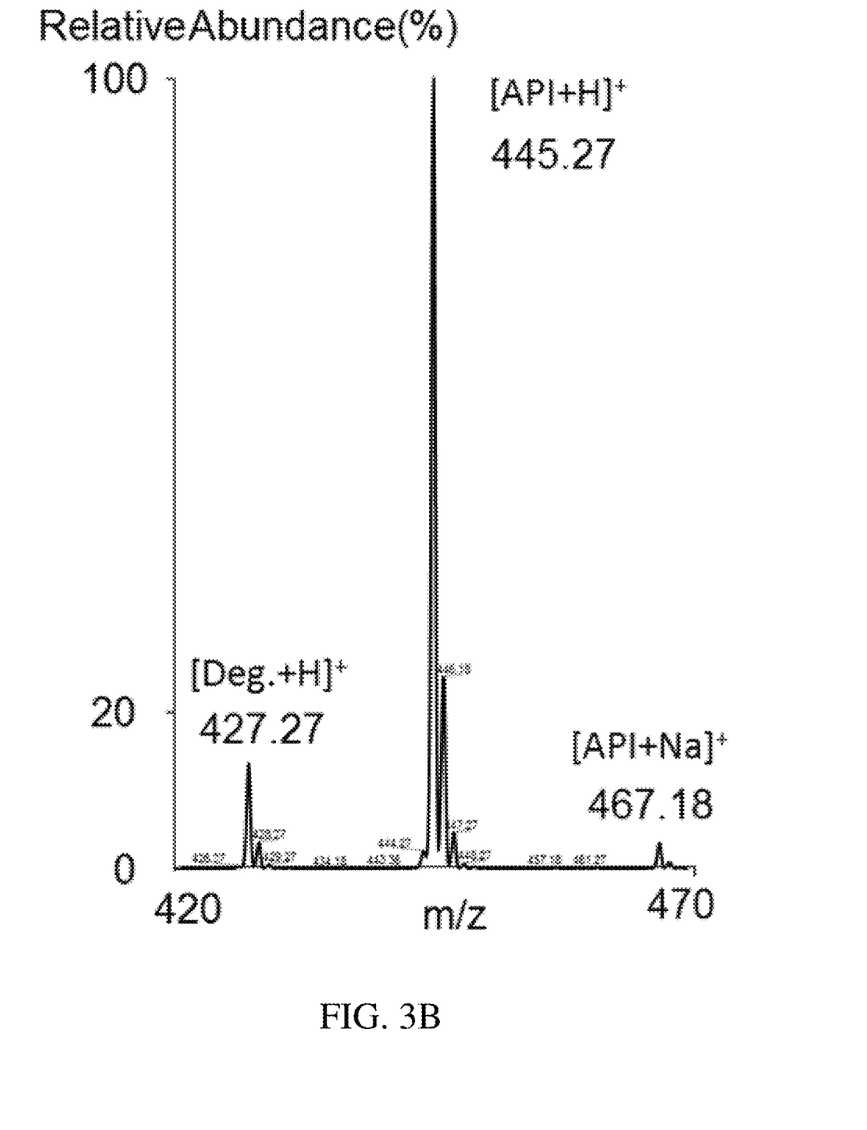

Besides the similarity in the kinetic profile, the mass spectra of the reacting system when recorded at particular times chosen to correspond to the same extent of degradation (FIGS. 3A-B) showed no significant differences, which confirms the reliability of Leidenfrost droplet reactors to accelerate this degradation reaction. It also indicates that nanospray MS alone can be adequate as a quick and reliable method for analyzing the degradation extent.

The data herein show that the acidic degradation of tetracycline has been accelerated to a factor of 180 in Leidenfrost droplets compared to the traditional bulk degradation, which indicates the value of using Leidenfrost droplets as an accelerated forced degradation method and of using nanospray MS alone to analyze the degradation product and measure the extent of conversion. This combination of accelerated reaction and analysis methodology could be used to investigate the stability of other APIs. Future prospects include further automation and multiplexing of the reaction so that an even faster method will be achieved to conduct forced degradation of APIs and more complex drug formulations.

Leidenfrost Droplets

Figure 4:
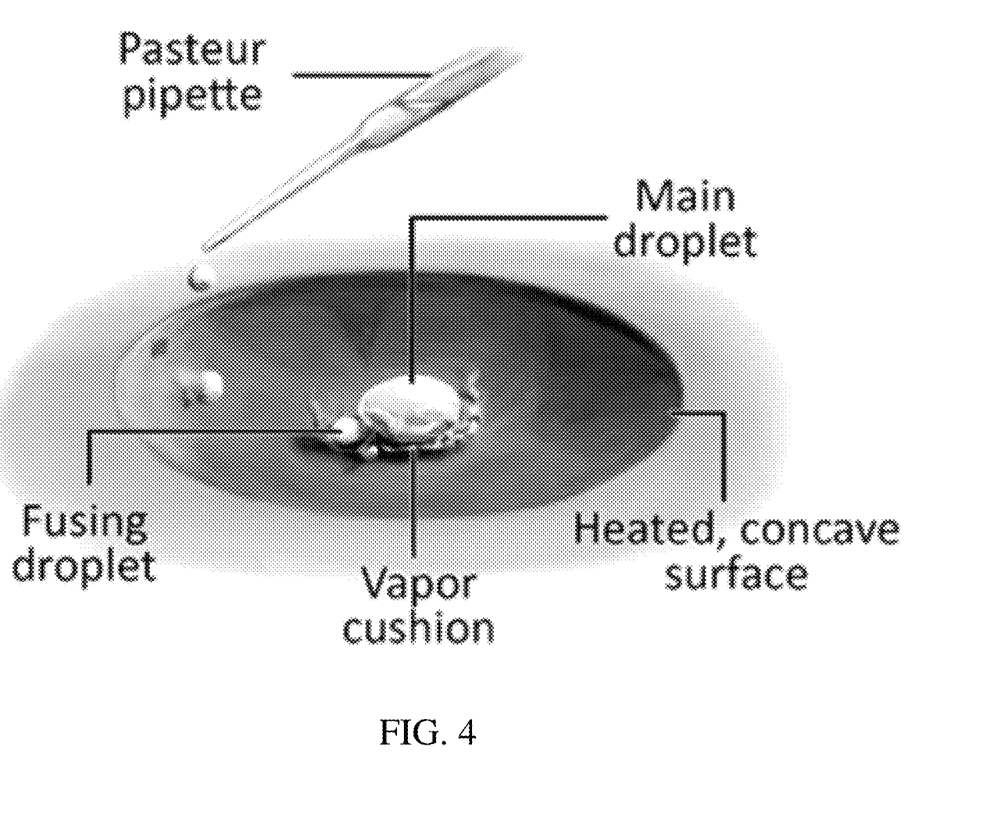
FIG. 4 shows a Leidenfrost reaction system used in methods of the invention in which additional reaction mixture is added via pipette to maintain constant volume Leidenfrost droplets. The added droplets impact the surface and fuse with the main levitated droplet which sits atop a cushion of solvent vapor.

Leidenfrost droplets and the Leidenfrost effect is described for example in Cooks et al. (U.S. patent application publication number 2017/0349547), the content of which is incorporated by reference herein in its entirety. As discussed above, aspects of the invention take advantage of the Leidenfrost effect. With reference to FIG. 4, the Leidenfrost effect occurs when a liquid is brought to a surface heated to a temperature significantly higher than the liquid's boiling point. As the droplet approaches the super-heated surface, an insulating vapor layer is formed that keeps the solution from boiling rapidly. With this vapor cushion in place, the droplet levitates on the surface and solvent gradually evaporates. In certain embodiments, the methods of the invention use the Leidenfrost effect to perform accelerated chemical reactions in droplets. In certain embodiments, the reaction is conducted while maintaining a substantially constant volume of the droplets. By maintaining Leidenfrost droplets at constant volume it is shown that acceleration is mainly due to interfacial effects. In other embodiments, the droplet reduces in volume as the reaction occurs and the reaction product is formed in a Leidenfrost droplet having a reduced volume.

Pneumatic Spraying

In other embodiments, pneumatic spraying may be used to produce the microdroplets. Pneumatic spraying techniques and devices are described for example in Cooks et al. (U.S. patent application publication number 2018/0043327), the content of which is incorporated by reference herein in its entirety. In general, the methods of the invention can include a spray system in which pneumatics and optionally electrical potential are used to create a fine spray, for example an electrosonic spray ionization source, such as described for example in Takats et al. (Anal. Chem., 2004, 76 (14), pp 4050-4058), the content of which is incorporated by reference herein in its entirety. The skilled artisan will recognize that any source that generates a liquid spray discharge including small droplets (e.g., microdroplets), charged or uncharged, can be used with systems and methods of the invention.

Additional exemplary ionization sources include techniques that utilize ionization sources at atmospheric pressure for mass spectrometry include electrospray ionization (ESI; Fenn et al., Science, 246:64-71, 1989; and Yamashita et al., J. Phys. Chem., 88:4451-4459, 1984); atmospheric pressure ionization (APCI; Carroll et al., Anal. Chem. 47:2369-2373, 1975); and atmospheric pressure matrix assisted laser desorption ionization (AP-MALDI; Laiko et al. Anal. Chem., 72:652-657, 2000; and Tanaka et al. Rapid Commun. Mass Spectrom., 2:151-153, 1988). The content of each of these references in incorporated by reference herein its entirety.

Other exemplary mass spectrometry techniques that work with systems and methods of the invention utilize direct ambient ionization/sampling methods that include direct analysis in real time (DART; Cody et al., Anal. Chem., 77:2297-2302, 2005); Atmospheric Pressure Dielectric Barrier Discharge Ionization (DBDI; Kogelschatz, Plasma Chemistry and Plasma Processing, 23:1-46, 2003, and PCT international publication number WO 2009/102766), and electrospray-assisted laser desorption/ionization (ELDI; Shiea et al., J. Rapid Communications in Mass Spectrometry, 19:3701-3704, 2005). The content of each of these references in incorporated by reference herein its entirety.

In certain embodiments, ions of a sample are generated using nanospray ESI. Exemplary nano spray tips and methods of preparing such tips are described for example in Wilm et al. (Anal. Chem. 2004, 76, 1165-1174), the content of which is incorporated by reference herein in its entirety. NanoESI is described for example in Karas et al. (Fresenius J Anal Chem. 2000 March-April; 366(6-7):669-76), the content of which is incorporated by reference herein in its entirety.

On-Line Reaction Monitoring

In certain embodiments, real-time analysis may be desirable. Accordingly, certain embodiments utilize on-line monitoring systems for monitoring the formation of a degradation product within a microdroplet. The volume of the droplet may be maintained as discussed above and the rate/amount of addition of solvent or reagents is determined by the rate and/or amount of liquid removed from the microdroplet in which the degradation reaction is occurring. The removed portion of liquid is directly transferred to the on-line monitoring system. The system may be equipped with a transfer line that couples to the microdroplet in which the degradation reaction is occurring.

An exemplary on-line monitoring system is described for example in Cooks et al. (U.S. Pat. No. 9,500,623), the content of which is incorporated by reference herein in its entirety. Briefly, a transfer line is positioned in proximity to the microdroplet in which the degradation reaction is occurring. A portion of the microdroplet in which the degradation reaction is occurring is transferred through the transfer line to an emitter-spray tip. Ionization may be produced by inductive electrospray ionization. A positive electrospray potential applied to an electrode near to but not in physical contact with the solution being sprayed or the emitter is pulsed repeatedly to produce strong electric fields of both polarities which result in bursts of charged droplets being emitted from the solution while avoiding direct physical contact between the high voltage and the reaction solution. Sheath gas may be used to help in the nebulization process and minimize size-variation in the droplets. Sample splitting was useful in accelerating the flow rate of sampling and decreasing the delay time while avoiding contamination of the MS inlet. Mass spectra recorded as a function of time give the desired kinetic information.

Ion Transfer

In certain embodiments, ionization of a degradation product within a microdroplet may be desirable at a location remote from where the microdroplet resides. In such embodiments, the generated degradation reaction product ions may be transferred using an ion transfer line to an analysis system, such as a mass spectrometer. Systems and methods of transferring ions are described, for example in Ouyang et al. (U.S. Pat. No. 8,410,431), the content of which is incorporated by reference herein in its entirety. Such devices generate a laminar gas flow that allows for efficient transfer of ions without significant loss of signal intensity over longer distances, such as distances of at least about 5 cm, at least about 10 cm, at least about 20 cm, at least about 50 cm, at least about 100 cm, at least about 500 cm, at least about 1 m, at least about 3 m, at least about 5 m, at least about 10 m, and other distances. Ion transfer devices of the invention are useful for chemical analysis in situations in which it is important for the ion focusing device or instrument and the object being examined to be in different locations. Generally, the ion transfer member is operably coupled to a gas flow generating device, in which the gas flow generating device produces a laminar gas flow that transfers the gas phase ions to an inlet of the ion focusing device.

Ion transfer devices of the invention provide enlarged flow to carry ions from a distant sample to the ion focusing device. The basic principle used in the transport device is the use of the gas flow to direct gas and ions into the ion transfer member and to form a laminar flow inside the ion transfer member to keep the ions away from the walls while transferring the gas and ions through the ion transfer member. The analyte ions of interest are sampled at some point downstream along the ion transfer member. The laminar flow is achieved by balancing the incoming and outgoing gas flow. Thus recirculation regions and/or turbulence are avoided. Thus, the generated laminar flow allows for high efficient ion transport over long distance or for sampling of ions over large areas.

Ion transfer devices of the invention also provide enlarged flow to carry ions from the ion source to the ion focusing device. Additional gas flow provided by a miniature sample pump connected with the ion transfer member facilitates ion transfer from an ambient ionization source to the vicinity of the ion focusing device.

As described in certain embodiments, an ion transfer member, e.g., a tube with an inner diameter of about 10 mm or greater, may be used to transfer ions from the ionization source to the ion focusing device. The larger opening of the ion transfer member, as compared to the opening of the inlet of the ion focusing device, is helpful for collection of sample ions generated in a large space, e.g. on a surface of large area. The large flow conductance of the ion transfer member allows the gas carrying ions to move toward the inlet of the ion analysis device at a fast flow rate. The ion transfer member is coupled to a gas flow generating device. The gas flow generating device produces a gas flow inside the ion transfer member. The inlet of the ion analysis device receives the ions transferred from the ambient ionization source.

The ion transfer member may be any connector that allows for production of a laminar flow within it and facilitates transfer of ions without significant loss of ion current. Exemplary ion transfer members include tubes, capillaries, covered channels, open channels, and others. In a particular embodiment, the ion transfer member is a tube. The ion transfer member may be composed of rigid material, such as metal or glass, or may be composed of flexible material such as plastics, rubbers, or polymers. An exemplary flexible material is TYGON® flexible polymer tubing (Saint-Gobain, Courbevoie, France).

The ion transfer member may be any shape as long the shape allows for the production of a flow to prevent the ions from reaching the internal surfaces of the ion transfer member where they might become neutral. For example, the ion transfer member may have the shape of a straight line. Alternatively, the ion transfer member may be curved or have multiple curves.

The ion transfer member is coupled to a gas flow generating device. The gas flow generating device is such a device capable of generating a gas flow through the ion transfer member. The gas flow generating device facilitates transfer of the ions from the ambient ionization source to the inlet of the ion analysis device. In certain embodiments, the gas flow generating device is a pump with a high flow rate and a low compression ratio. An example of such a pump is that found in a shop vacuum or a small sample pump. The proper pumps used for the coupling are different from those used for a mass spectrometer, e.g. a rotary vane pump or a turbo molecular pump, which pumps have a high compression ratio. The high compression ratio pumps of a mass spectrometer cannot be connected to the atmosphere through an opening of the conductance described here. For example, Cotte-Rodriguez et al. (Chem. Commun., 2006, 2968-2970) describe a set-up in which the inlet of the mass spectrometer was elongated and gas flow generated by the pump inside a mass spectrometer was used to transfer ions over a distance up to 1 m. The ions were transferred from the atmosphere to a region at about 1 torr. A significant loss in signal occurred for the transfer of the ions using the set-up described in Cotte-Rodriguez, and ions generated over a large area could not be efficiently collected into the inlet.

In other embodiments, the gas flow generating device is the ambient ionization source. For example, a source used for desorption electrospray ionization (DESI) generates a gas flow sufficient to produce a laminar flow through the ion transfer member, and thus produces a laminar gas flow that transfers the gas phase ions over a long distance to an inlet of the ion analysis device.

Numerous additional devices may be coupled with the ion transfer member to further facilitate transfer of the ions from the ambient ionization source to the inlet of the ion focusing device. For example, an electric lens may be used to focus the ions toward the center of the ion transfer member while the gas flow generating device pumps away neutral gases. In other embodiments, an electro-hydrodynamic lens system may be implemented to use the air dynamic effects to focus the heavier particles and to use the electric field to focus the charged particles toward the center of the ion transfer member.

In other embodiments, a distal end of the ion transfer member may include a plurality of inlets for transferring ions from multiple locations to the inlet of the ion focusing device. In still other embodiments, the ion transfer member includes additional features to prevent ions from being adsorbed onto the inside wall. For example, a dielectric barrier discharge (DBD) tubing is made from a double stranded speaker wire. The insulator of the wire serves as the dielectric barrier and the DBD occurs when high voltage AC is applied between the two strands of the wire. The DBD inside the tube prevents the ions from adsorbing onto the wall and provide a charge-enriched environment to keep the ions in the gas phase. This DBD tube can also be used for ionizing the gas samples while transferring the ions generated to the inlet of the ion focusing device. The DBD tube can also be used for ion reactions while transferring the ions generated to the inlet of the ion focusing device.

System Architecture

In certain embodiments, the systems and methods of the invention can be carried out using automated systems and computing devices. Specifically, aspects of the invention described herein can be performed using any type of computing device, such as a computer, that includes a processor, e.g., a central processing unit, or any combination of computing devices where each device performs at least part of the process or method. In some embodiments, systems and methods described herein may be controlled using a handheld device, e.g., a smart tablet, or a smart phone, or a specialty device produced for the system.

Systems and methods of the invention can be performed using software, hardware, firmware, hardwiring, or combinations of any of these. Features implementing functions can also be physically located at various positions, including being distributed such that portions of functions are implemented at different physical locations (e.g., imaging apparatus in one room and host workstation in another, or in separate buildings, for example, with wireless or wired connections).

Processors suitable for the execution of computer program include, by way of example, both general and special purpose microprocessors, and any one or more processor of any kind of digital computer. Generally, a processor will receive instructions and data from a read-only memory or a random access memory or both. The essential elements of computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, solid state drive (SSD), and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having an I/O device, e.g., a CRT, LCD, LED, or projection device for displaying information to the user and an input or output device such as a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected through network by any form or medium of digital data communication, e.g., a communication network. For example, the reference set of data may be stored at a remote location and the computer communicates across a network to access the reference set to compare data derived from the female subject to the reference set. In other embodiments, however, the reference set is stored locally within the computer and the computer accesses the reference set within the CPU to compare subject data to the reference set. Examples of communication networks include cell network (e.g., 3G or 4G), a local area network (LAN), and a wide area network (WAN), e.g., the Internet.

The subject matter described herein can be implemented as one or more computer program products, such as one or more computer programs tangibly embodied in an information carrier (e.g., in a non-transitory computer-readable medium) for execution by, or to control the operation of, data processing apparatus (e.g., a programmable processor, a computer, or multiple computers). A computer program (also known as a program, software, software application, app, macro, or code) can be written in any form of programming language, including compiled or interpreted languages (e.g., C, C++, Perl), and it can be deployed in any form, including as a stand-alone program or as a module, component, subroutine, or other unit suitable for use in a computing environment. Systems and methods of the invention can include instructions written in any suitable programming language known in the art, including, without limitation, C, C++, Perl, Java, ActiveX, HTML5, Visual Basic, or JavaScript.

A computer program does not necessarily correspond to a file. A program can be stored in a file or a portion of file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

A file can be a digital file, for example, stored on a hard drive, SSD, CD, or other tangible, non-transitory medium. A file can be sent from one device to another over a network (e.g., as packets being sent from a server to a client, for example, through a Network Interface Card, modem, wireless card, or similar).

Writing a file according to the invention involves transforming a tangible, non-transitory computer-readable medium, for example, by adding, removing, or rearranging particles (e.g., with a net charge or dipole moment into patterns of magnetization by read/write heads), the patterns then representing new collocations of information about objective physical phenomena desired by, and useful to, the user. In some embodiments, writing involves a physical transformation of material in tangible, non-transitory computer readable media (e.g., with certain optical properties so that optical read/write devices can then read the new and useful collocation of information, e.g., burning a CD-ROM). In some embodiments, writing a file includes transforming a physical flash memory apparatus such as NAND flash memory device and storing information by transforming physical elements in an array of memory cells made from floating-gate transistors. Methods of writing a file are well-known in the art and, for example, can be invoked manually or automatically by a program or by a save command from software or a write command from a programming language.

Suitable computing devices typically include mass memory, at least one graphical user interface, at least one display device, and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks (DVD) or other optical storage, magnetic cassettes, magnetic tape, magnetic disk storage or other magnetic storage devices, Radiofrequency Identification tags or chips, or any other medium which can be used to store the desired information and which can be accessed by a computing device.

As one skilled in the art would recognize as necessary or best-suited for performance of the methods of the invention, a computer system or machines of the invention include one or more processors (e.g., a central processing unit (CPU) a graphics processing unit (GPU) or both), a main memory and a static memory, which communicate with each other via a bus.

Figure 5:
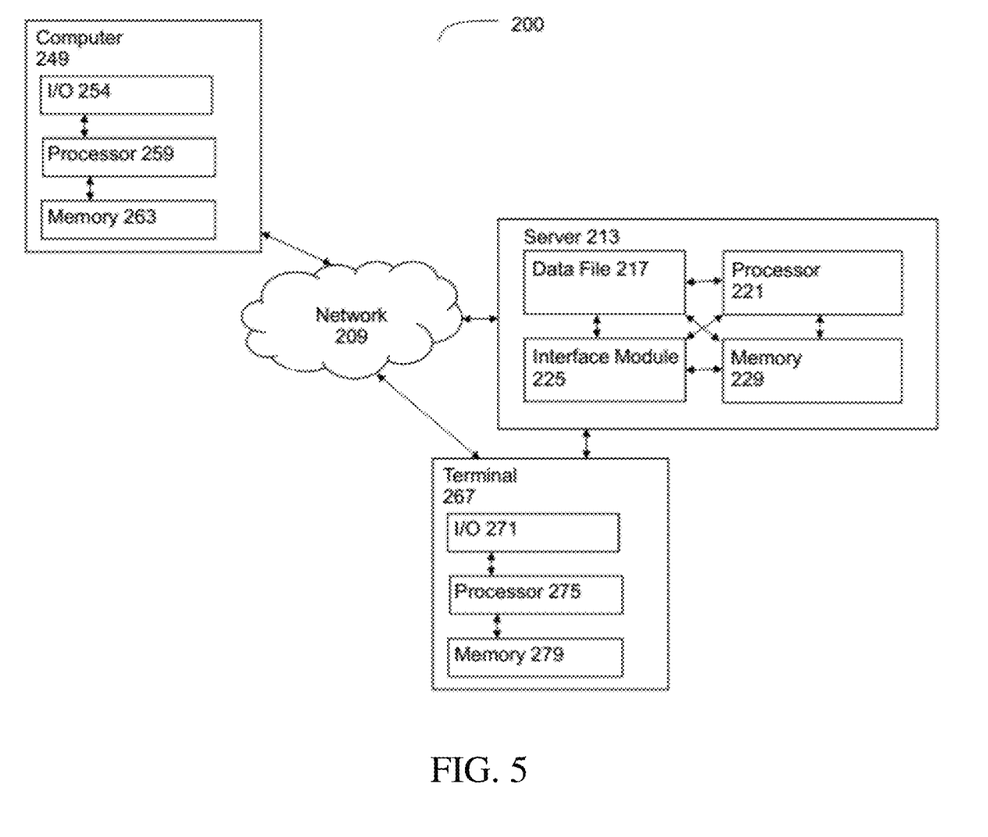
FIG. 5 is an illustration showing an exemplary data analysis module for implementing the systems and methods of the invention in certain embodiments.

In an exemplary embodiment shown in FIG. 5, system 200 can include a computer 249 (e.g., laptop, desktop, or tablet). The computer 249 may be configured to communicate across a network 209. Computer 249 includes one or more processors 259 and memory 263 as well as an input/output mechanism 254. Where methods of the invention employ a client/server architecture, an steps of methods of the invention may be performed using server 213, which includes one or more of processors 221 and memory 229, capable of obtaining data, instructions, etc., or providing results via interface module 225 or providing results as a file 217. Server 213 may be engaged over network 209 through computer 249 or terminal 267, or server 213 may be directly connected to terminal 267, including one or more processors 275 and memory 279, as well as input/output mechanism 271.

System 200 or machines according to the invention may further include, for any of I/O 254 or 271 a video display unit (e.g., a liquid crystal display (LCD) or a cathode ray tube (CRT)). Computer systems or machines according to the invention can also include an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

Memory 263, 279, or 229 according to the invention can include a machine-readable medium on which is stored one or more sets of instructions (e.g., software) embodying any one or more of the methodologies or functions described herein. The software may also reside, completely or at least partially, within the main memory and/or within the processor during execution thereof by the computer system, the main memory and the processor also constituting machine-readable media. The software may further be transmitted or received over a network via the network interface device.

Ion Analysis

Figure 6:
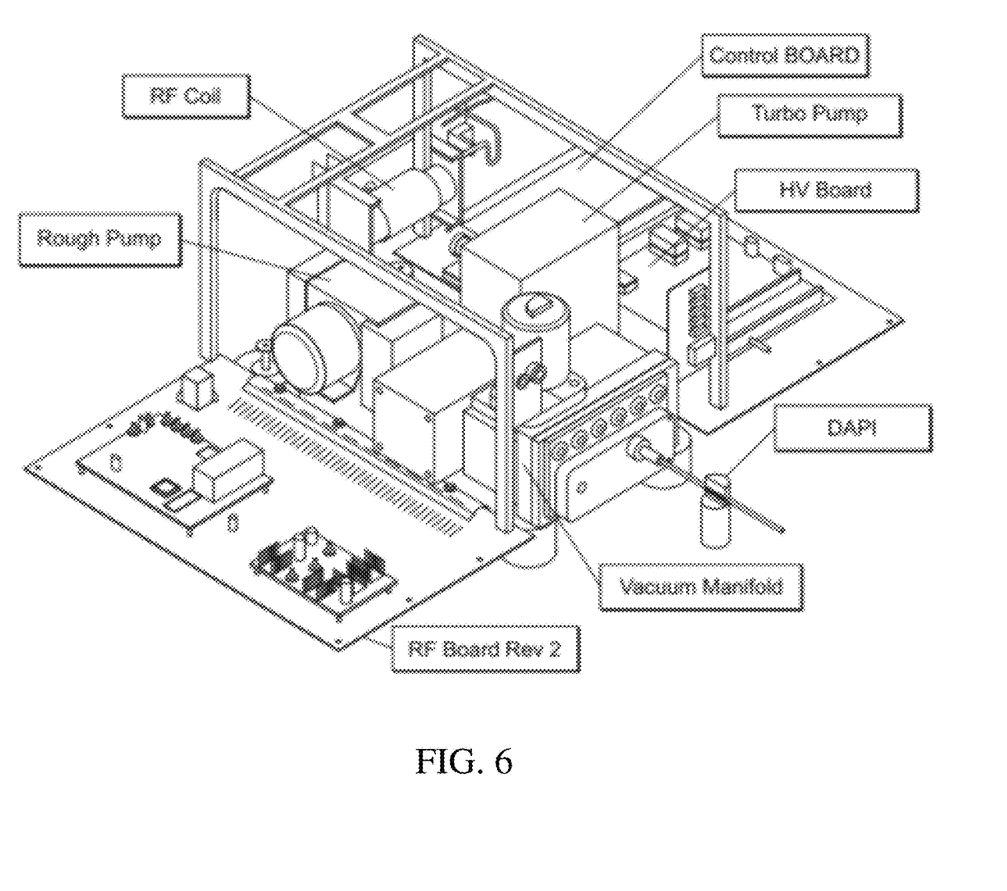
FIG. 6 is a picture illustrating various components and their arrangement in a miniature mass spectrometer.

In certain embodiments, the ions are analyzed by directing them into a mass spectrometer (bench-top or miniature mass spectrometer). FIG. 6 is a picture illustrating various components and their arrangement in a miniature mass spectrometer. The control system of the Mini 12 (Linfan Li, Tsung-Chi Chen, Yue Ren, Paul I. Hendricks, R. Graham Cooks and Zheng Ouyang "Miniature Ambient Mass Analysis System" Anal. Chem. 2014, 86 2909-2916, DOI: 10.1021/ac403766c; and 860. Paul I. Hendricks, Jon K. Dalgleish, Jacob T. Shelley, Matthew A. Kirleis, Matthew T. McNicholas, Linfan Li, Tsung-Chi Chen, Chien-Hsun Chen, Jason S. Duncan, Frank Boudreau, Robert J. Noll, John P. Denton, Timothy A. Roach, Zheng Ouyang, and R. Graham Cooks "Autonomous in-situ analysis and real-time chemical detection using a backpack miniature mass spectrometer: concept, instrumentation development, and performance" Anal. Chem., 2014, 86 2900-2908 DOI: 10.1021/ac403765x, the content of each of which is incorporated by reference herein in its entirety), and the vacuum system of the Mini 10 (Liang Gao, Qingyu Song, Garth E. Patterson, R. Graham Cooks and Zheng Ouyang, "Handheld Rectilinear Ion Trap Mass Spectrometer", Anal. Chem., 78 (2006) 5994-6002 DOI: 10.1021/ac061144k, the content of which is incorporated by reference herein in its entirety) may be combined to produce the miniature mass spectrometer shown in FIG. 6. It may have a size similar to that of a shoebox (H20×W25 cm×D35 cm). In certain embodiments, the miniature mass spectrometer uses a dual LIT configuration, which is described for example in Owen et al. (U.S. patent application Ser. No. 14/345,672), and Ouyang et al. (U.S. patent application Ser. No. 61/865,377), the content of each of which is incorporated by reference herein in its entirety.

The mass spectrometer (miniature or benchtop), may be equipped with a discontinuous interface. A discontinuous interface is described for example in Ouyang et al. (U.S. Pat. No. 8,304,718) and Cooks et al. (U.S. patent application publication number 2013/0280819), the content of each of which is incorporated by reference herein in its entirety.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for analyzing stability of an active pharmaceutical agent, the method comprising:
   obtaining an active pharmaceutical ingredient;
   distributing the active pharmaceutical agent into one or more droplets, wherein a plurality of the one or more droplets are each at least one or more millimeters in size;
   subjecting the one or more droplets comprising the active pharmaceutical ingredient to one or more conditions that force degradation of the active pharmaceutical agent in each of the one or more droplets, wherein the one of more conditions that force degradation of the active pharmaceutical ingredient are selected from the group consisting of: acid addition, base addition, addition of an agent that causes radical initiation, peroxide addition, and a combination thereof; and
   analyzing the one or more droplets to determine a ratio of the active pharmaceutical ingredient to amount of a degradation product of the active pharmaceutical ingredient, thereby analyzing stability of an active pharmaceutical ingredient.

2. The method according to claim 1, wherein the one or more droplets are Leidenfrost-levitated droplets.

3. The method according to claim 2, wherein the one or more droplets are Leidenfrost-levitated droplets maintained at a constant volume.

4. The method according to claim 3, wherein the one or more Leidenfrost-levitated droplets are maintained at a constant volume by introducing droplets of pure solvent to the Leidenfrost-levitated droplets.

5. The method according to claim 4, wherein a rate at which the droplets of the pure solvent are introduced to the Leidenfrost-levitated droplets is dependent on an evaporation rate of the Leidenfrost-levitated droplets.

6. The method according to claim 1, wherein analyzing the one or more droplets to determine a ratio of the active pharmaceutical ingredient to presence of a degradation product of the active pharmaceutical ingredient is by a mass spectrometry technique.

7. The method according to claim 6, wherein the method further comprises determining an acceleration factor of degradation of the active pharmaceutical ingredient in the one or more droplets by measuring time required to convert the active pharmaceutical agent to a fixed amount of the degradation product as determined by peak intensities in a mass spectrum compared to corresponding time for a bulk forced degradation of the active pharmaceutical ingredient.

8. The method according to claim 1, wherein the method further comprises determining an acceleration factor of degradation of the active pharmaceutical ingredient in the one or more droplets by measuring of a rate constant for conversion of the active pharmaceutical ingredient to degradation products compared to a corresponding rate constant for a bulk forced degradation of the active pharmaceutical ingredient.

9. The method according to claim 1, wherein the one or more droplets are generated by a pneumatic spray device.

10. A method for analyzing stability of a formulation that comprises an active pharmaceutical ingredient, the method comprising:
    obtaining a formulation that comprises an active pharmaceutical ingredient;
    distributing the formulation that comprises the active pharmaceutical ingredient into one or more droplets, wherein a plurality of the one or more droplets are each at least one or more millimeters in size;
    subjecting the one or more droplets comprising the formulation that comprises the active pharmaceutical ingredient to one or more conditions that force degradation of the formulation that comprises the active pharmaceutical ingredient in each of the one or more droplets; and
    analyzing the one or more droplets to determine a ratio of the active pharmaceutical ingredient in the formulation to presence of a degradation product of the active pharmaceutical ingredient in the formulation, thereby analyzing stability of an active pharmaceutical ingredient.

11. The method according to claim 10, further comprising determining whether the formulation that comprises the active pharmaceutical ingredient slows degradation of the active pharmaceutical ingredient as compared to a different formulation that comprises the active pharmaceutical ingredient.

12. The method according to claim 10, wherein the one or more droplets are Leidenfrost-levitated droplets.

13. The method according to claim 12, wherein the one or more Leidenfrost-levitated droplets are maintained at a constant volume.

14. The method according to claim 13, wherein the one or more droplets are Leidenfrost-levitated droplets are maintained at a constant volume by introducing droplets of pure solvent to the Leidenfrost-levitated droplets.

15. The method according to claim 14, wherein a rate at which the droplets of the pure solvent are introduced to the Leidenfrost-levitated droplets is dependent on an evaporation rate of the Leidenfrost-levitated droplets.

16. The method according to claim 15, wherein analyzing the one or more droplets to determine a ratio of the active pharmaceutical agent to presence of a degradation product of the active pharmaceutical ingredient in the formulation is by a mass spectrometry technique.

17. The method according to claim 15, wherein the method further comprises determining an acceleration factor of degradation of the active pharmaceutical ingredient in the formulation in the one or more droplets by measuring time required to convert the active pharmaceutical ingredient in the formulation to a fixed amount of the degradation product as determined by peak intensities in a mass spectrum compared to corresponding time for a bulk forced degradation of the active pharmaceutical ingredient in the formulation.

18. The method according to claim 10, wherein the method further comprises determining an acceleration factor of degradation of the active pharmaceutical ingredient in the formulation in the one or more droplets by measuring of a rate constant for conversion of the active pharmaceutical ingredient in the formulation to degradation products compared to a corresponding rate constant for a bulk forced degradation of the active pharmaceutical ingredient in the formulation.

19. The method according to claim 10, wherein the one or more droplets are generated by a pneumatic spray device.

* * * * *